US005633348A

United States Patent [19]
Johann et al.

[11] Patent Number: 5,633,348
[45] Date of Patent: May 27, 1997

[54] AMPHOTROPIC VIRUS RECEPTOR

[75] Inventors: Stephen V. Johann, Pearl River; Marja van Zeijl, Cornwall; Bryan M. O'Hara, Pearl River, all of N.Y.

[73] Assignee: American Cyanamid Company, Madison, N.J.

[21] Appl. No.: 582,719

[22] Filed: Jan. 4, 1996

Related U.S. Application Data

[62] Division of Ser. No. 50,684, Apr. 16, 1993, Pat. No. 5,550,221.

[51] Int. Cl.$^6$ ............... C07K 14/435; C12N 15/12
[52] U.S. Cl. ............... 530/350; 530/395; 435/69.1
[58] Field of Search .................... 530/350, 395; 435/69.1

[56] References Cited

U.S. PATENT DOCUMENTS 5,550,221  8/1996  Johann et al. ............... 536/23.5

OTHER PUBLICATIONS

Sommerfelt, MA et al, Receptor Interference Groups of 20 Retroviruses Plating on Human Cells, Virology, vol. 176, No. 1, pp. 58–69, 1990.

Handelin, B. L., et al., Cell Surface Receptors for Murine Leukemia viruses: Two Assays and Their Implications, Virology, vol. 140, No. 1, pp. 183–187 (1985).

Kawakami, T.G., et al., Antigenic Studies on Gibbon Type–C Viruses, Transplantation Proceedings, Vo. VI, No. 2 (Jun.), pp. 193–196, 1974.

Kawakami, T.G., et al., Letters to Nature, Nature New Biology, vol. 235, pp. 170–171, (1972).

Kawakami, T.G., et al., Onocogenicity of Gibbon Type–C Myelogenous Leukemia Virus, Int. J. Cancer: 25, 641–646 (1980).

Sanger, F., et al., DNA sequencing with chain–terminating inhibitors, Proc. Natl. Acad Sco, USA, vol. 74, No. 12, pp. 5463–5467, 1977.

O'Hara, B., et al., Characterization of a Human Gene Conferring Sensitivity to Infection by Gibbon Ape Leukemia Virus, Cell Growth & Differentiation, vol. 1: 119–127, 1990.

Kaelbling, M. et al., Localization of the Human Gene Allowing Infection by Gibbon Ape Leukemia Virus to Human Chromosome Region 2q11–q14 and to the Homologous Region on Mouse Chromosome 2, Journal of Virology, vol. 65, No. 4, pp. 1743–1747 (1991).

Garcia, J. V., et a l., Localization of the Amphotropic Murine Leukemia Virus Receptor Gene to the Pericentromeric Region of Human Chromosome 8, Journal of Virology, vol. 65, No. 11, pp. 6316–6319, 1991.

Macleod et al., Mol. Cell. Biol. vol. 10, p. 3663, 1990.

Primary Examiner—Stephen Walsh
Assistant Examiner—Sally P. Teng
Attorney, Agent, or Firm—Karen A. Lowney; Elizabeth M. Barnhard

[57] ABSTRACT

The present invention relates to an isolated nucleic acid fragment comprising a nucleic acid sequence coding for an amphotropic retrovirus receptor. This receptor is referred to as GLVR2 and has approximately 62% homology with the GLVR1 gene encoding for Gibbon Ape Leukemia Virus (GALV). Differences for the type of retroviruses interacting with the receptors exist. The protein encoding by the GLVR2 gene, cells transformed or transfected by the gene and vectors containing the gene are also disclosed.

2 Claims, 3 Drawing Sheets

```
CAGATCGGGA AGAAAAATAT GGAATGTGTT TTACCGCTGA CTGAACACAA CCAAATGAAC    60
TGTCCTGACA GTAGTTTGCA AACCAGCAGC TAGCAGTTTG TCCAGCCTCT AACATTGTCC   120
AGCACTTTCC AGAGCAAACT CACTGTTTAC AAGAACTCTT GGCCTTACGA AGTTTATAAC   180
CTCAAGCTTT GTTTATTTAA AATATTCCTG CAAAAGAAAA GTACCCGGCA CCCACTTTCC   240
AAAATGGCCA TGGATGAGTA TTTGTGGATG GTCATTTGG GTTTCATCAT AGCTTTCATC    300
TTGGCCTTTT CTGTTGGTGC AAACGATGTT GCCAACTCCT TTGGTACAGC CGTGGGCTCT   360
GGTGTGGTGA CCTTGAGGCA GGCATGCATT TTAGCTTCAA TATTTGAAAC CACCGGCTCC   420
GTGTTACTAG GCGCCAAAGT AGGAGAAACC ATTCGCAAAG GTATCATTGA CGTGAACCTG   480
TACAACGAGA CGGTGGAGAC TCTCATGGCT GGGGAAGTTA GTGCCATGGT TGGTTCCGCT   540
GTGTGGCAGC TGATTGCTTC CTTCCTGAGG CTTCCAATCT CAGGAACGCA CTGCATTGTG   600
GGTTCTACTA TAGGATTCTC ACTGGTCGCA ATCGGTACCA AAGGTGTGCA GTGGATGGAG   660
CTTGTCAAGA TTGTTGCTTC TTGGTTTATA TCTCCACTGT TGTCTGGTTT CATGTCTGGC   720
CTGCTGTTTG TACTCATCAG AATTTTCATC TTAAAAAAGG AAGACCCTGT TCCCAATGGC   780
CTCCGGGCAC TCCAGTATT CTATGCTGCT ACCATAGCAA TCAATGTCTT TTCCATCATG   840
TACACAGGAG CACCAGTGCT CGGCCTTGTT CTCCCCATGT GGGCCATAGC CCTCATTTCC   900
TTTGGTGTCG CCCTCCTGTT CGCTTTTTTT GTGTGGCTCT TCGTGTGTCC GTGGATGCGG   960
AGGAAAATAA CAGGCAAATT ACAAAAAGAA GGTGCTTTAT CACGAGTATC TGACGAAAGC  1020
CTCAGTAAGG TTCAGGAAGC AGAGTCCCCA GTATTTAAAG AGCTACCAGG TGCCAAGGCT  1080
AATGATGACA GCACCATCCC GCTCACGGGA GCAGCAGGGG AGACACTGGG GACCTCGGAA  1140
GGCACTTCTG CGGGCAGCCA CCCTCGGGCT GCATACGGAA GAGCACTGTC CATGACCCAT  1200
GGCTCTGTGA AATCGCCCAT CTCCAACGGC ACCTTCGGCT TCGACGGCCA CACCAGGAGC  1260
GACGGTCATG TGTACCACAC CGTGCACAAA GACTCGGGGC TCTACAAAGA TCTGCTGCAC  1320
AAAATCCACA TCGACAGGGG CCCCGAGGAG AAGCCAGCCC AGGAAAGCAA CTACCGGCTG  1380
CTCCGCCGAA ACAACAGTTA CACCTGCTAC ACCGCAGCCA TTTGTGGGCT GCCAGTGCAC  1440
GCCACCTTTC GAGCTGCGGA CTCATCGGCC CCAGAGGACA GTGAGAAGCT GGTGGGCGAC  1500
ACCGTGTCCT ACTCCAAGAA GAGGCTGCGC TACGACAGCT ACTCGAGCTA CTGTAACGCG  1560
GTGGCAGAGG CGGAGATCGA GGCGGAGGAG GGCGGCGTGG AGATGAAGCT GGCGTCGGAG  1620
CTGGCCGACC CTGACCAGCC GCGAGAGGAC CCTGCAGAGG AGGAGAAGGA GGAGAAGGAC  1680
GCACCCGAGG TTCACCTCCT GTTCCATTTC CTGCAGGTCC TCACCGCCTG TTTCGGGTCC  1740
TTTGCTCACG GCGGCAATGA CGTGAGTAAT GCCATCGGTC CCTGGTAGC CTTGTGGCTG   1800
ATTTACAAAC AAGGCGGGGT AACGCAAGAA GCAGCTACAC CCGTCTGGCT GCTGTTTTAT  1860
GGAGGAGTTG GAATCTGCAC AGGCCTCTGG GTCTGGGGGA GAAGAGTGAT CCAGACCATG  1920
GGGAAGGACC TCACTCCCAT CACGCCGTCC AGCGGCTTCA CGATCGAGCT GGCCTCAGCC  1980
TTCACAGTGG TGATCGCCTC CAACATCGGG CTTCCAGTCA GCACCACGCA CTGTAAGGTG  2040
```

FIG.1A

```
GGCTCGGTGG TGGCCGTGGG CTGGATCCGC TCCCGCAAGG CTGTGGACTG GCGCCTCTTT  2100
CGGAACATCT TCGTGGCCTG GTTCGTGACC GTCCCTGTGG CTGGGCTGTT CAGCGCTGCT  2160
GTCATGGCTC TTCTCATGTA TGGGATCCTT CCATATGTGT GATTTGTCTT CTTCCAGCTG  2220
CAAACAGCTA AAGGGATGGT CTGGTGTTGG CGTGTGGGAG ACATGTGTGC TCGTGCCGCA  2280
CATACACATC CTGGCCGTGC ACGGCTCTCT CATGACCAGC TCTCTGCCTC CCTTCCAGGA  2340
GGCTCCATCC CACACTGTTC ACCCAGGCTG CGGAGACTCA CCTTCCCGAG CTAACTTAAC  2400
TACTGTACAT AATAATATGT ATTAAACTGG TATCGTGGTG ATATAATGTG GTGCAGTTAC  2460
TTATATATTA AATATCTATT GTATCCATAG AATAGGCAGC ATTATTTCAA ACATATTCAA  2520
GTTGGGAGTG GAGATCATTG CCTAGAAGTC AATATTCAAT AAATCTTGTA CATAACTATT  2580
TCGATGGCAA ATGTTAAGCC TTCTAAAAGG AAAGTGTAGA TTGGAAAATG ATTTTTTTTC  2640
CAAATGATGT TTTTGCCTTC TAATATACTG TAAGGTAATG AGCTTCAGAA CAGGCAACCT  2700
GACCCTGCAG AGGTCGCGTG CTGTGGGATG ACAGCGGGAC GGGAGCTCAC AAGTGCTTTC  2760
ACTGAAGATT TGTTCATATA CTGTGTATTG ATTGTTGTGT AATATATCAT CATTGCTTTT  2820
GTAAATACGT AAAACTGTAA TTTTTTAATG GTGTGCTTCC CTTATACTTT TTGATCAGAG  2880
AATTTTGGAA AGTACCAAAG AAGCAGGGGA ATCATTGGCC AGTGTTACGT TTTCACATTG  2940
TCTGTCTCCC ACCCTCACTG ATCACGCCTG CCCCAGAGCA GTGTGTGGCG GTGACACCGT  3000
CACCCAGCAT GCGCCACGCC GTCGTCCCAC CAGCAGTGCC ACCGCCACCA CACCCCAGAT  3060
CCCACCCACC TTGCAGTGGC TTTCTTGTCA TCAGAGTAGA GAATGCACAG GTGTTGGTGA  3120
GGGCGTGTGG CTGAGCACTA CATGTCAAGT CAGAGTCAGT TTCTATCCAA TTCTC        3175
```

FIG.1B

```
MAMDEYLVMVILGFIIAFILAFSVGANDVANSFGTAVGSGVVTLRQACILASIFETTGSV   60

LLGAKVGETIRKGIIDVNLYNETVETLMAGEVSAMVGSAVWQLIASFLRLPISGTHCIYG  120

STIGFSLVAIGTKGVQWMELVKIVASWFISPLLSGFMSGLLFVLIRIFILKKEDPVPNGL  180

RALPVFYAATIAINVFSIMYTGAPVLGLVLPMWAIALISFGVALLFAFFVWLFVCPVMRR  240

KITGKLQKEGALSRVSDESLSKVQEAESPVFKELPGAKANDDSTIPLTGAAGETLGTSEG  300

TSAGSHPRAAYGRALSMTHGSVKSPISNGTFGFDGHTRSDGHVYHTVHKDSGLYKDLLHK  360

IHIDRGPEEKPAQESNYRLLRRNNSYTCYTAAICGLPVHATFRAADSSAPEDSEKLVGDT  420

VSYSKKRLRYDSYSSYCNAVAEAEIEAEEGGVEMKLASELADPDQPREDPAEEEKEEKDA  480

PEVHLLFHFLQVLTACFGSFAHGGNDVSNAIGPLVALWLIYKQGGVTQEAATPVWLLFYG  540

GVGICTGLWVWGRRVIQTMGKDLTPITPSSGFTIELASAFTVVIASNIGLPVSTTHCKVG  600

SVVAVGWIRSRKAVDWRLFRNIFVAWFVTVPVAGLFSAAVMALLMYGILPYV.         652
```

FIG. 2

AMPHOTROPIC VIRUS RECEPTOR

This is a divisional of application Ser. No. 08/050,684 filed on Apr. 16, 1993, now U.S. Pat. No. 5,550,221.

Following the discovery of human immunodeficiency virus and human T-cell leukemia virus, the study of unrecognized frequent infection of humans and other mammals by retroviruses has been more actively studied. Of particular interest is the study of how retroviruses achieve infection. It is generally understood that the initial stage of infection requires an interaction between a glycoprotein of the retrovirus envelope and a receptor on the surface of the intended host's cells. It is known that different retroviruses utilize different receptors in infecting host cells, and the absence of the appropriate retroviral receptor on the cell of a particular species will prevent infection by that retrovirus. Interference studies indicate that there are probably no more than eight different retrovirus receptors for retroviruses known to infect human cells (Sommerfelt and Weiss, Virology, 176:58–69, 1990). Many retroviruses can infect human cells in vitro, but the role of such viruses in causing disease, if any, has yet to be elucidated. The study of the retrovirus life cycle is hampered by a lack of knowledge of the identity and structure of the various retroviral receptors, and the extent of their expression in human and other potential host cells.

One recently identified receptor is that for Gibbon Ape Leukemia Virus (GALV; U.S. Pat. No. 5,151,361). GALV is known to cause myeloid leukemias in gibbons, and has been isolated from animals with lymphosarcoma and granulocyte leukemia (Kawakamira and Buckley, Transplant Proc., 6:193–196, 1984; Kawakami et al., Nature (London) New Biol., 235:170–171, 1972, Kawakami et al., Int. J. Cancer, 25:841–846, 1980). Although there is no known disease caused by this virus in humans, its receptor (GLVR1) is expressed in human cells. In addition to acting as the receptor for GALV, this receptor is also utilized by another retrovirus, Feline Leukemia Virus-B (FeLV-B).

It has now been unexpectedly determined that a gene highly homologous, but not identical, to the GALV receptor exists. This gene is designated as GLVR2. Most surprisingly, however, the gene is determined to encode yet another functionally distinct retroviral receptor, namely the receptor for amphotropic retroviruses. Amphotropic retroviruses comprise a distinct group of murine viruses with a wide host range. They infect most mammalian cells, including human.

SUMMARY OF THE INVENTION

The present invention provides an isolated nucleic acid fragment comprising a nucleic acid sequence encoding an amphotropic retrovirus receptor, hereinafter referred to as GLVR2, and is approximately homologous to the GLVR1 gene that encodes the GALV receptor. However, the two receptors encoded by the different genes are sufficiently distinct so as to serve as receptors for different types of retroviruses. It is determined that GALV cannot use GLVR2 as a receptor, that is, mouse NIH 3T3 cells transfected with an expression plasmid for GLVR 2 cannot be infected with GALV, whereas Chinese hamster ovary cells transfected with the same plasmid become infectable with amphotropic virus. Similarly, given this observation, it is expected that amphotropic virus will be unable to use GLVR1 as a receptor, because the receptors map to physically distinct locations in the human genome (Kaelbling et al., J. Virol., 65:1743–1747, 1991; García et al., J. Virol., 65:6316–6319, 1991) and because the viruses do not interfere in human cells (Sommerfelt and Weiss, Virology, 176:58–69, 1990).

The fragment can also be used to create vectors for transformation of host cells to express the GLVR2 gene and receptor protein. The invention also provides probes, in the form of the nucleic acid fragment or portions thereof, which have been detectably labelled. Such probes are useful in the study of receptor distribution in cells of various species and/or tissue types. Amphotropic virus vectors are currently the standard for human gene therapy. Determination of the levels of GLVR2 expression in target cells or tissues is therefore useful in assessing the potential for successful gene delivery. Comparison to GLVR1 levels is useful in deciding which of the two vector systems should be used. As demonstrated here by the isolation of GLVR2 using GLVR1 as a probe in low stringency screening of recombinant libraries, both GLVR1 and -2 are useful for the isolation of further GLVR-like sequences from various species.

Also provided are recombinantly expressed a amphotropic receptor proteins, and antibodies raised there-to.

BRIEF DESCRIPTION OF THE FIGURES

FIG. 1 shows the DNA sequence of GLVR2 cDNA (SEQ ID NO: 1; a composite of clones 1 and 9). The ATG and TGA delineating the open reading frame homologous to GLVR1 are underlined.

FIG. 2 shows the a mino acid sequence (SEQ ID NO: 2) encoded by the cDNA depicted in FIG. 1.

DETAILED DESCRIPTION OF THE INVENTION

Four hundred thousand plagues from a human HL60 cell cDNA library are screened under low stringency conditions with a cDNA fragment containing the human GLVR1 sequence. After two washes, about 20 positive plaques are picked and purified. Two clones are identified as containing GLVR1 related sequence, but neither clone contains a full-length coding region. An additional 350,000 plaques from a human placenta cDNA library are screened under high stringency condition. An additional eight plaques are identified. Digestion of rescued plasmids shows inserts ranging from 0.6–3.7 kb. A larger clone (about 2.7 kb) is sequenced and found to be missing about 0.5 kb of the 5' coding sequence relative to the GLVR1 sequence. The cDNA library is again screened with a 300 bp fragment of this positive clone at high stringency, resulting in 9 clones, at least one of which contains a full GLVR2 sequence homologous to the GLVR1 open reading frame. The isolated clone is approximately 5.5 kb, with an open reading frame of 1956 bases, producing a full-length protein of 652 amino acids in length. The nucleotide and amino acid sequence are depicted respectively in FIGS. 1 and 2. The identity of the gene as encoding an amphotropic virus receptor is confirmed by the observation that CHO cells, which are normally resistant to infection by murine amphotropic virus, upon transfection with a GLVR2 containing vector, become infectable.

The conclusively identified clone is then used in Southern hybridization to identify the presence of homologues in DNA derived from other species. Homologous genes are shown to be present in monkey, rat, dog, cow, rabbit and chicken, but not in yeast cells.

Southern analysis of a panel of human-mouse hybrid cells is used to map the chromosomal location of GLVR2. This procedure shows that GLVR2 maps to human chromosome 8, in contrast with GLVR1, which maps to human chromosome 2.

The novel nucleic acid fragments provide a useful tool for the study of retroviruses. The fragment encoding the receptor, or portions thereof, can be detectably labelled (e.g., with a radioisotope) and used as a probe to identify and isolate GLVR2 homologues from a variety of species. This can be readily achieved by screening genomic or cDNA libraries under conditions of low stringency and thereby isolating novel GLVR-related sequences. If these clones do not encode full-length GLVR proteins, they can be used as probes in turn to isolate full-length clones. Therefore, the "isolated nucleic acid fragment" claimed herein also is intended to encompass nucleic acid fragments which hybridize with a nucleic acid sequence encoding the amino acid sequence of FIG. 2, wherein the nucleic acid fragment encodes a functional amphotropic receptor. By encoding a functional receptor, it is meant that when transfected into a cell previously resistant to amphotropic virus infection, the cell is thereby rendered infectable.

Isolated GLVR2 fragments can be used to express the receptor in a variety of host cells, both prokaryotic and eukaryotic. Examples of suitable eukaryotic cells include mammalian cells, plant cells, yeast cells, and insect cells. Suitable prokaryotic hosts include *Escherichia coli* and *Bacillus subtilis*.

Suitable expression vectors are selected based upon the choice of host cell. Numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular mammalian cells are commonly transformed with SV40, polyoma virus, or transfected with plasmids such as pRC/CNV; and insect cells in culture may be transformed with baculovirus expression vectors. Yeast vector systems include yeast centromere plasmids, yeast episomal plasmids and yeast integrating plasmids. The invention encompasses any and all host cells transformed or transfected by the claimed nucleic acid fragments, as well as expression vectors used to achieve this.

In one specific application, the receptor DNA can be expressed in cell lines normally resistant to infection by a particular retrovirus. The transfected cell is then contacted with that retrovirus, to determine if it has been rendered infectable. If infection is achieved after transfection, GLVR2 will have been demonstrated to encode the receptor for that virus.

In another embodiment, the receptor gene is used to express the protein in a bacterial host. Protein expressed in bacteria can be used in raising antisera (both polyclonal and monoclonal) by standard methodology. Such antibodies are useful in immunohistochemical studies to determine the level of expression of the receptor protein in various tissues and cell lines. The receptor can be purified from bacterial cells if found in inclusion bodies, for example, by isolation of inclusion bodies by standard techniques, followed by electrophoresis in BDS-PAGE gels and isolation of the protein band from the gel. Alternately, the long hydrophilic region (residues 236–482 in the human protein) can be expressed as a fusion protein, e.g., with glutathione-s-transferase, or maltose binding protein, and then purified by isolation of the protein to which it is fused.

Alternately, the predicted amino acid sequence can be used to design synthetic peptides unique to the amphotropic receptor, which peptides can then be used to raise antibodies to the receptors.

Amphotropic virus vectors are currently the only ones used for human gene therapy. Knowledge of expression levels for the amphotropic receptor is therefore important. Isolation of the receptor may lead to a better understanding of how the virus and receptor interact and may lead to improved modalities for gene therapy.

Also, the nucleic acid fragment, or portions thereof, can be used as a probe to isolate other genes in the GLVR family. The data provided herein demonstrate that there is more than one GLVR gene, and given this observation, it is predicted that GLVR genes other than GLVR1 and 2 also exist. In particular, since the envelope glycoprotein of xenotropic retroviruses is homologous to the amphotropic and FeLV-B envelope glycoprotein, but these viruses do not use the same receptors, the homology suggests the use of a receptor homologous to GLVR1 and 2. Thus, the predicted xenotropic virus receptor, herein designated GLVR3, can be isolated using either GLVR1 or 2 as a probe, in the same manner as described herein for GLVR2 isolation. Identity of isolated clones can be confirmed by sequencing and expression also described herein.

It will be understood by those skilled in the art that the invention is not limited to the specific nucleotide and amino acid sequences depicted in FIGS. 1 and 2: in addition to the human GLVR2 sequence depicted therein, the invention also encompasses modifications to the sequence, such as deletions, insertions, or substitutions in the sequence which produce silent changes in the resulting protein molecule. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. In some cases, it may in fact be desirable to make mutants of the sequence in order to study the effect of alteration on the biological activity of the protein. Each of the proposed modifications is well within the routine skill in the art, as is determination of retention of biological activity of the encoded products.

The invention is further described in the following non-limiting examples.

EXAMPLES

1. Isolation of cDNAs for GLVR2

400,000 plaques from a human cDNA library made from HL60 cells (Clontech #1020b) are screened at low stringency with two EcoRI fragments containing bases 1–2659 for the human GLVR1 cDNA-containing clone pHGR6-1 (O'Hara et al., 1990). The screening is carried out in 50% formamide, 5× SSC, 10×Denhardt's 0.1% SDS, and 100 µg/ml salmon sperm DNA, at 30° C. The filters are washed in 0.2× SSC, 0.2% SDS at 45° C. for 20 minutes and exposed to film for 3 days. The filters are then rewashed in the same solution at 65° C. for 30 minutes and exposed to film. About 40 plaques are detected after the first wash, but only about 20 after the second. The first set of plaques are picked and plaque-purified using the less stringent conditions. Two clones, OJ40A and OJ40B, make it through this procedure and contain GLVR1-related sequences as determined by DNA sequencing. Because these clones contain only several hundred bases related to the GLVR1 codon region, efforts are made to isolate full-length clones. To do this, 350,000 plaques from a human placenta cDNA library (Stratagene, 936203) are screened using a 1 kb BamHI fragment of OJ40B at high stringency (hybridization is in the above hybridization solution at 42° C.; washing is at a final stringency of 0.2% SDS, 0.2× SSC, 65° C.). The eight positive plaques are rescued from the λ zap vector using the manufacturer's protocol. EcoRI digests of the rescued plasmids reveal insert sizes ranging from 0.6–3.7 kb. One of the largest clones (#9, ~2.7 kb) is sequenced in its entirety using synthetic primers and the dideoxy chain termination method on double stranded templates (Sanger et al., PNAS USA, 74:5463–5467, 1977). Compared to GLVR1 sequence, this clone is missing 0.5 kb of the 5' coding sequence. The cDNA library is then screened with the 5' 300 bp HindIII-NcoI fragment of clone 9 at high stringency, resulting in 9 clones, at least one of which contains the full GLVR2 sequence homologous to the open reading frame of GLVR1 (clone 1, 5.5 kb).

2. Southern Analysis

A Southern blot (containing DNAs from various species and purchased from Clontech) is hybridized in the hybridization solution described above at 30° C. with the HindIII-NcoI fragment of clone 1 as probe. The blot is washed at a final stringency of 0.2% SDS, 0.2× SSC at 40° C. The result shows the presence of a homologous gene in monkey, rat, dog, cow, rabbit, and chicken, but not in yeast.

3. Chromosomal mapping of GLVR2

The chromosomal location of GLVR2 is determined using Southern Analysis of a panel of human-mouse hybrid cells (which tend to lose human chromosomes with time in culture) and the 1 kb BamHI fragment of pOJ40B as probe. In this widely used system, described in Kaelbling et al. (J. Virology, 65:1743–1747, 1991), hybrids are first characterized cytogenetically for which human chromosomes they contain. Southern analysis is then used to determine which of the hybrids carry the gene being mapped. A table is then drawn up showing concordancy between the presence of the gene and the presence of a specific human chromosome. In this way, GLVR2 is shown to map to human chromosome 8.

4. Expression of GLVR2

In order to construct an expression plasmid for GLVR2, the following steps are taken. pcDNA-tkpA, constructed by Dr. Tom Jones, Lederle Laboratories, is derived from pcDNA1 (In Vitrogen). For convenience in manipulation, the ampicillin resistance gene is cloned into pcDNA1 by cloning in a blunt 1.1 kb fragment from pBR322 encoding $Amp^R$ into the NruI site of pcDNA1 between supF and the cytomegalovirus (CMV) immediate early promoter. The 1.23 kb XbaI-AccI fragment (containing the splice, polyadenylation signal, and SP6 promoter) is removed, the vector filled in with Klenow, and a 180 bp BamHI-HaeIII fragment (filled in with Klenow) containing the Herpes simplex virus thymidine kinase polyadenylation signal, is inserted. To clone GLVR2 into this plasmid, the HindIII-SacI fragment of pGLVR2-1 (nucleotides 184–2745 in FIG. 1 containing the complete open reading frame with 59 untranslated nucleotides upstream of the open reading frame and 543 untranslated nucleotides downstream of the open reading frame) is cloned between the HindIII and EcoRV sites of pcDNA1-tkpA. The clone is designated pOJ74. This clone, when introduced into Chinese hamster ovary cells, confers susceptibility to infection by recombinant retroviruses with murine leukemia virus gag-pol proteins and amphotropic envelope glycoprotein. Susceptibility is conferred by relieving a receptor block because the same (untransfected) cells are normally infectable by a virus with the same gag-pol proteins, but containing gibbon ape leukemia virus envelope glycoprotein.

DEPOSIT OF BIOLOGICAL MATERIALS

The following biological materials have been deposited with the American Type Culture Collection, 12301 Parklawn Drive, Rockville, Md., under the Budapest Treaty, on Apr. 1, 1993 and given the indicated Accession Numbers:

| Description | Accession No. |
| --- | --- |
| pOJ74/E. coli DH5α (containing GLVR2) | ATCC 69274 |

What we claim is:

1. A recombinantly produced amphotropic virus receptor protein comprising the amino acid sequence as set forth in SEQ ID NO: 2.

2. A recombinantly produced amphotropic virus receptor protein encoded by the nucleic acid molecule having the nucleic acid sequence set forth in SEQ ID NO: 1.

* * * * *

UNITED STATES PATENT AND TRADEMARK OFFICE
CERTIFICATE OF CORRECTION

PATENT NO. : 5,633,348

DATED : May 27, 1997

INVENTOR(S) : Stephen Vincent Johann, et al.

It is certified that error appears in the above-identified patent and that said Letters Patent is hereby corrected as shown below:

Title Page, Right Column, line 5: change "Sco.", to --Sci.--.
Col. 1, line 50: after "approximately", add --62%--.
Col. 2, line 29: change "plagues" to --plaques--.
Col. 3, line 55: change "BDS-PAGE" to --SDS-PAGE--.

Signed and Sealed this

Twenty-sixth Day of October, 1999

Attest:

Q. TODD DICKINSON

*Attesting Officer*  Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3175 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:

( A ) NAME/KEY: CDS
( B ) LOCATION: 244..2202

( x i ) SEQUENCE DESCRIPTION: SEQ ID NO:1:

```
CAGATCGGGA AGAAAAATAT GGAATGTGTT TTACCGCTGA CTGAACACAA CCAAATGAAC        60

TGTCCTGACA GTAGTTTGCA AACCAGCAGC TAGCAGTTTG TCCAGCCTCT AACATTGTCC       120

AGCACTTTCC AGAGCAAACT CACTGTTTAC AAGAACTCTT GGCCTTACGA AGTTTATAAC       180

CTCAAGCTTT GTTTATTTAA AATATTCCTG CAAAAGAAAA GTACCCGGCA CCCACTTTCC       240
```

| | | | | | | | | | | | | | | | |
|---|---|---|---|---|---|---|---|---|---|---|---|---|---|---|---|
| AAA | ATG | GCC | ATG | GAT | GAG | TAT | TTG | TGG | ATG | GTC | ATT | TTG | GGT | TTC | ATC | 288 |
| | Met | Ala | Met | Asp | Glu | Tyr | Leu | Trp | Met | Val | Ile | Leu | Gly | Phe | Ile | |
| | 1 | | | | 5 | | | | | 10 | | | | | 15 | |

| ATA | GCT | TTC | ATC | TTG | GCC | TTT | TCT | GTT | GGT | GCA | AAC | GAT | GTT | GCC | AAC | 336 |
|---|---|---|---|---|---|---|---|---|---|---|---|---|---|---|---|---|
| Ile | Ala | Phe | Ile | Leu | Ala | Phe | Ser | Val | Gly | Ala | Asn | Asp | Val | Ala | Asn | |
| | | | | 20 | | | | | 25 | | | | | 30 | | |

| TCC | TTT | GGT | ACA | GCC | GTG | GGC | TCT | GGT | GTG | GTG | ACC | TTG | AGG | CAG | GCA | 384 |
|---|---|---|---|---|---|---|---|---|---|---|---|---|---|---|---|---|
| Ser | Phe | Gly | Thr | Ala | Val | Gly | Ser | Gly | Val | Val | Thr | Leu | Arg | Gln | Ala | |
| | | | 35 | | | | | 40 | | | | | 45 | | | |

| TGC | ATT | TTA | GCT | TCA | ATA | TTT | GAA | ACC | ACC | GGC | TCC | GTG | TTA | CTA | GGC | 432 |
|---|---|---|---|---|---|---|---|---|---|---|---|---|---|---|---|---|
| Cys | Ile | Leu | Ala | Ser | Ile | Phe | Glu | Thr | Thr | Gly | Ser | Val | Leu | Leu | Gly | |
| | | 50 | | | | | 55 | | | | | 60 | | | | |

| GCC | AAA | GTA | GGA | GAA | ACC | ATT | CGC | AAA | GGT | ATC | ATT | GAC | GTG | AAC | CTG | 480 |
|---|---|---|---|---|---|---|---|---|---|---|---|---|---|---|---|---|
| Ala | Lys | Val | Gly | Glu | Thr | Ile | Arg | Lys | Gly | Ile | Ile | Asp | Val | Asn | Leu | |
| 65 | | | | | 70 | | | | | 75 | | | | | | |

| TAC | AAC | GAG | ACG | GTG | GAG | ACT | CTC | ATG | GCT | GGG | GAA | GTT | AGT | GCC | ATG | 528 |
|---|---|---|---|---|---|---|---|---|---|---|---|---|---|---|---|---|
| Tyr | Asn | Glu | Thr | Val | Glu | Thr | Leu | Met | Ala | Gly | Glu | Val | Ser | Ala | Met | |
| 80 | | | | | 85 | | | | | 90 | | | | | 95 | |

| GTT | GGT | TCC | GCT | GTG | TGG | CAG | CTG | ATT | GCT | TCC | TTC | CTG | AGG | CTT | CCA | 576 |
|---|---|---|---|---|---|---|---|---|---|---|---|---|---|---|---|---|
| Val | Gly | Ser | Ala | Val | Trp | Gln | Leu | Ile | Ala | Ser | Phe | Leu | Arg | Leu | Pro | |
| | | | | 100 | | | | | 105 | | | | | 110 | | |

| ATC | TCA | GGA | ACG | CAC | TGC | ATT | GTG | GGT | TCT | ACT | ATA | GGA | TTC | TCA | CTG | 624 |
|---|---|---|---|---|---|---|---|---|---|---|---|---|---|---|---|---|
| Ile | Ser | Gly | Thr | His | Cys | Ile | Val | Gly | Ser | Thr | Ile | Gly | Phe | Ser | Leu | |
| | | | 115 | | | | | 120 | | | | | 125 | | | |

| GTC | GCA | ATC | GGT | ACC | AAA | GGT | GTG | CAG | TGG | ATG | GAG | CTT | GTC | AAG | ATT | 672 |
|---|---|---|---|---|---|---|---|---|---|---|---|---|---|---|---|---|
| Val | Ala | Ile | Gly | Thr | Lys | Gly | Val | Gln | Trp | Met | Glu | Leu | Val | Lys | Ile | |
| | | 130 | | | | | 135 | | | | | 140 | | | | |

| GTT | GCT | TCT | TGG | TTT | ATA | TCT | CCA | CTG | TTG | TCT | GGT | TTC | ATG | TCT | GGC | 720 |
|---|---|---|---|---|---|---|---|---|---|---|---|---|---|---|---|---|
| Val | Ala | Ser | Trp | Phe | Ile | Ser | Pro | Leu | Leu | Ser | Gly | Phe | Met | Ser | Gly | |
| 145 | | | | | 150 | | | | | 155 | | | | | | |

| CTG | CTG | TTT | GTA | CTC | ATC | AGA | ATT | TTC | ATC | TTA | AAA | AAG | GAA | GAC | CCT | 768 |
|---|---|---|---|---|---|---|---|---|---|---|---|---|---|---|---|---|
| Leu | Leu | Phe | Val | Leu | Ile | Arg | Ile | Phe | Ile | Leu | Lys | Lys | Glu | Asp | Pro | |
| 160 | | | | | 165 | | | | | 170 | | | | | 175 | |

| GTT | CCC | AAT | GGC | CTC | CGG | GCA | CTC | CCA | GTA | TTC | TAT | GCT | GCT | ACC | ATA | 816 |
|---|---|---|---|---|---|---|---|---|---|---|---|---|---|---|---|---|
| Val | Pro | Asn | Gly | Leu | Arg | Ala | Leu | Pro | Val | Phe | Tyr | Ala | Ala | Thr | Ile | |
| | | | 180 | | | | | 185 | | | | | 190 | | | |

| GCA | ATC | AAT | GTC | TTT | TCC | ATC | ATG | TAC | ACA | GGA | GCA | CCA | GTG | CTC | GGC | 864 |
|---|---|---|---|---|---|---|---|---|---|---|---|---|---|---|---|---|
| Ala | Ile | Asn | Val | Phe | Ser | Ile | Met | Tyr | Thr | Gly | Ala | Pro | Val | Leu | Gly | |
| | | | 195 | | | | | 200 | | | | | 205 | | | |

| CTT | GTT | CTC | CCC | ATG | TGG | GCC | ATA | GCC | CTC | ATT | TCC | TTT | GGT | GTC | GCC | 912 |
|---|---|---|---|---|---|---|---|---|---|---|---|---|---|---|---|---|
| Leu | Val | Leu | Pro | Met | Trp | Ala | Ile | Ala | Leu | Ile | Ser | Phe | Gly | Val | Ala | |
| | | 210 | | | | | 215 | | | | | 220 | | | | |

| CTC | CTG | TTC | GCT | TTT | TTT | GTG | TGG | CTC | TTC | GTG | TGT | CCG | TGG | ATG | CGG | 960 |
|---|---|---|---|---|---|---|---|---|---|---|---|---|---|---|---|---|
| Leu | Leu | Phe | Ala | Phe | Phe | Val | Trp | Leu | Phe | Val | Cys | Pro | Trp | Met | Arg | |
| 225 | | | | | 230 | | | | | 235 | | | | | | |

| AGG | AAA | ATA | ACA | GGC | AAA | TTA | CAA | AAA | GAA | GGT | GCT | TTA | TCA | CGA | GTA | 1008 |
|---|---|---|---|---|---|---|---|---|---|---|---|---|---|---|---|---|
| Arg | Lys | Ile | Thr | Gly | Lys | Leu | Gln | Lys | Glu | Gly | Ala | Leu | Ser | Arg | Val | |
| 240 | | | | | 245 | | | | | 250 | | | | | 255 | |

| TCT | GAC | GAA | AGC | CTC | AGT | AAG | GTT | CAG | GAA | GCA | GAG | TCC | CCA | GTA | TTT | 1056 |
|---|---|---|---|---|---|---|---|---|---|---|---|---|---|---|---|---|
| Ser | Asp | Glu | Ser | Leu | Ser | Lys | Val | Gln | Glu | Ala | Glu | Ser | Pro | Val | Phe | |
| | | | | 260 | | | | | 265 | | | | | 270 | | |

| | | | | | | | | | | | | | | | | |
|---|---|---|---|---|---|---|---|---|---|---|---|---|---|---|---|---|
| AAA | GAG | CTA | CCA | GGT | GCC | AAG | GCT | AAT | GAT | GAC | AGC | ACC | ATC | CCG | CTC | 1104 |
| Lys | Glu | Leu | Pro 275 | Gly | Ala | Lys | Ala | Asn 280 | Asp | Asp | Ser | Thr | Ile 285 | Pro | Leu | |
| ACG | GGA | GCA | GCA | GGG | GAG | ACA | CTG | GGG | ACC | TCG | GAA | GGC | ACT | TCT | GCG | 1152 |
| Thr | Gly | Ala | Ala 290 | Gly | Glu | Thr | Leu | Gly 295 | Thr | Ser | Glu | Gly | Thr 300 | Ser | Ala | |
| GGC | AGC | CAC | CCT | CGG | GCT | GCA | TAC | GGA | AGA | GCA | CTG | TCC | ATG | ACC | CAT | 1200 |
| Gly | Ser 305 | His | Pro | Arg | Ala | Ala 310 | Tyr | Gly | Arg | Ala | Leu 315 | Ser | Met | Thr | His | |
| GGC | TCT | GTG | AAA | TCG | CCC | ATC | TCC | AAC | GGC | ACC | TTC | GGC | TTC | GAC | GGC | 1248 |
| Gly 320 | Ser | Val | Lys | Ser | Pro 325 | Ile | Ser | Asn | Gly | Thr 330 | Phe | Gly | Phe | Asp | Gly 335 | |
| CAC | ACC | AGG | AGC | GAC | GGT | CAT | GTG | TAC | CAC | ACC | GTG | CAC | AAA | GAC | TCG | 1296 |
| His | Thr | Arg | Ser | Asp 340 | Gly | His | Val | Tyr | His 345 | Thr | Val | His | Lys | Asp 350 | Ser | |
| GGG | CTC | TAC | AAA | GAT | CTG | CTG | CAC | AAA | ATC | CAC | ATC | GAC | AGG | GGC | CCC | 1344 |
| Gly | Leu | Tyr | Lys 355 | Asp | Leu | Leu | His | Lys 360 | Ile | His | Ile | Asp | Arg 365 | Gly | Pro | |
| GAG | GAG | AAG | CCA | GCC | CAG | GAA | AGC | AAC | TAC | CGG | CTG | CTC | CGC | CGA | AAC | 1392 |
| Glu | Glu | Lys | Pro 370 | Ala | Gln | Glu | Ser | Asn 375 | Tyr | Arg | Leu | Leu | Arg 380 | Arg | Asn | |
| AAC | AGT | TAC | ACC | TGC | TAC | ACC | GCA | GCC | ATT | TGT | GGG | CTG | CCA | GTG | CAC | 1440 |
| Asn | Ser 385 | Tyr | Thr | Cys | Tyr | Thr 390 | Ala | Ala | Ile | Cys | Gly 395 | Leu | Pro | Val | His | |
| GCC | ACC | TTT | CGA | GCT | GCG | GAC | TCA | TCG | GCC | CCA | GAG | GAC | AGT | GAG | AAG | 1488 |
| Ala 400 | Thr | Phe | Arg | Ala | Ala 405 | Asp | Ser | Ser | Ala | Pro 410 | Glu | Asp | Ser | Glu | Lys 415 | |
| CTG | GTG | GGC | GAC | ACC | GTG | TCC | TAC | TCC | AAG | AAG | AGG | CTG | CGC | TAC | GAC | 1536 |
| Leu | Val | Gly | Asp | Thr 420 | Val | Ser | Tyr | Ser | Lys 425 | Lys | Arg | Leu | Arg | Tyr 430 | Asp | |
| AGC | TAC | TCG | AGC | TAC | TGT | AAC | GCG | GTG | GCA | GAG | GCG | GAG | ATC | GAG | GCG | 1584 |
| Ser | Tyr | Ser | Ser 435 | Tyr | Cys | Asn | Ala | Val 440 | Ala | Glu | Ala | Glu | Ile 445 | Glu | Ala | |
| GAG | GAG | GGC | GGC | GTG | GAG | ATG | AAG | CTG | GCG | TCG | GAG | CTG | GCC | GAC | CCT | 1632 |
| Glu | Glu | Gly | Gly 450 | Val | Glu | Met | Lys | Leu 455 | Ala | Ser | Glu | Leu | Ala 460 | Asp | Pro | |
| GAC | CAG | CCG | CGA | GAG | GAC | CCT | GCA | GAG | GAG | GAG | AAG | GAG | GAG | AAG | GAC | 1680 |
| Asp | Gln | Pro | Arg 465 | Glu | Asp | Pro | Ala | Glu 470 | Glu | Glu | Lys | Glu | Glu 475 | Lys | Asp | |
| GCA | CCC | GAG | GTT | CAC | CTC | CTG | TTC | CAT | TTC | CTG | CAG | GTC | CTC | ACC | GCC | 1728 |
| Ala 480 | Pro | Glu | Val | His | Leu 485 | Leu | Phe | His | Phe | Leu 490 | Gln | Val | Leu | Thr | Ala 495 | |
| TGT | TTC | GGG | TCC | TTT | GCT | CAC | GGC | GGC | AAT | GAC | GTG | AGT | AAT | GCC | ATC | 1776 |
| Cys | Phe | Gly | Ser | Phe 500 | Ala | His | Gly | Gly | Asn 505 | Asp | Val | Ser | Asn | Ala 510 | Ile | |
| GGT | CCC | CTG | GTA | GCC | TTG | TGG | CTG | ATT | TAC | AAA | CAA | GGC | GGG | GTA | ACG | 1824 |
| Gly | Pro | Leu | Val 515 | Ala | Leu | Trp | Leu | Ile 520 | Tyr | Lys | Gln | Gly | Gly 525 | Val | Thr | |
| CAA | GAA | GCA | GCT | ACA | CCC | GTC | TGG | CTG | CTG | TTT | TAT | GGA | GGA | GTT | GGA | 1872 |
| Gln | Glu | Ala | Ala 530 | Thr | Pro | Val | Trp | Leu 535 | Leu | Phe | Tyr | Gly | Gly 540 | Val | Gly | |
| ATC | TGC | ACA | GGC | CTC | TGG | GTC | TGG | GGG | AGA | AGA | GTG | ATC | CAG | ACC | ATG | 1920 |
| Ile | Cys 545 | Thr | Gly | Leu | Trp | Val 550 | Trp | Gly | Arg | Arg | Val 555 | Ile | Gln | Thr | Met | |
| GGG | AAG | GAC | CTC | ACT | CCC | ATC | ACG | CCG | TCC | AGC | GGC | TTC | ACG | ATC | GAG | 1968 |
| Gly | Lys | Asp | Leu | Thr 560 | Pro | Ile | Thr | Pro | Ser 565 | Ser | Gly | Phe | Thr | Ile 570 | Glu 575 | |
| CTG | GCC | TCA | GCC | TTC | ACA | GTG | GTG | ATC | GCC | TCC | AAC | ATC | GGG | CTT | CCA | 2016 |
| Leu | Ala | Ser | Ala | Phe 580 | Thr | Val | Val | Ile | Ala 585 | Ser | Asn | Ile | Gly | Leu 590 | Pro | |

|  |  |  |  |  |  |  |  |  |  |  |  |  |  |  |  |
|---|---|---|---|---|---|---|---|---|---|---|---|---|---|---|---|
| GTC | AGC | ACC | ACG | CAC | TGT | AAG | GTG | GGC | TCG | GTG | GTG | GCC | GTG | GGC | TGG | 2064 |
| Val | Ser | Thr | Thr<br>595 | His | Cys | Lys | Val | Gly<br>600 | Ser | Val | Val | Ala | Val<br>605 | Gly | Trp |
| ATC | CGC | TCC | CGC | AAG | GCT | GTG | GAC | TGG | CGC | CTC | TTT | CGG | AAC | ATC | TTC | 2112 |
| Ile | Arg | Ser | Arg<br>610 | Lys | Ala | Val | Asp | Trp<br>615 | Arg | Leu | Phe | Arg | Asn<br>620 | Ile | Phe |
| GTG | GCC | TGG | TTC | GTG | ACC | GTC | CCT | GTG | GCT | GGG | CTG | TTC | AGC | GCT | GCT | 2160 |
| Val | Ala | Trp<br>625 | Phe | Val | Thr | Val<br>630 | Pro | Val | Ala | Gly | Leu<br>635 | Phe | Ser | Ala | Ala |
| GTC | ATG | GCT | CTT | CTC | ATG | TAT | GGG | ATC | CTT | CCA | TAT | GTG | TGATTTGTCT | 2209 |
| Val<br>640 | Met | Ala | Leu | Leu | Met<br>645 | Tyr | Gly | Ile | Leu | Pro<br>650 | Tyr | Val |

```
TCTTCCAGCT GCAAACAGCT AAAGGGATGG TCTGGTGTTG GCGTGTGGGA GACATGTGTG    2269
CTCGTGCCGC ACATACACAT CCTGGCCGTG CACGGCTCTC TCATGACCAG CTCTCTGCCT    2329
CCCTTCCAGG AGGCTCCATC CCACACTGTT CACCCAGGCT GCGGAGACTC ACCTTCCCGA    2389
GCTAACTTAA CTACTGTACA ATAATAATATG TATTAAACTG GTATCGTGGT GATATAATGT   2449
GGTGCAGTTA CTTATATATT AAATATCTAT TGTATCCATA GAATAGGCAG CATTATTTCA    2509
AACATATTCA AGTTGGGAGT GGAGATCATT GCCTAGAAGT CAATATTCAA TAAATCTTGT    2569
ACATAACTAT TTCGATGGCA AATGTTAAGC CTTCTAAAAG GAAAGTGTAG ATTGGAAAAT    2629
GATTTTTTTT CCAAATGATG TTTTTGCCTT CTAATATACT GTAAGGTAAT GAGCTTCAGA    2689
ACAGGCAACC TGACCCTGCA GAGGTCGCGT GCTGTGGGAT GACAGCGGGA CGGGAGCTCA    2749
CAAGTGCTTT CACTGAAGAT TTGTTCATAT ACTGTGTATT GATTGTTGTG TAATATATCA    2809
TCATTGCTTT TGTAAATACG TAAAACTGTA ATTTTTAAT GGTGTGCTTC CCTTATACTT     2869
TTTGATCAGA GAATTTTGGA AAGTACCAAA GAAGCAGGGG AATCATTGGC CAGTGTTACG    2929
TTTTCACATT GTCTGTCTCC CACCCTCACT GATCACGCCT GCCCAGAGC AGTGTGTGGC     2989
GGTGACACCG TCACCCAGCA TGCGCCACGC CGTCGTCCCA CCAGCAGTGC CACCGCCACC    3049
ACACCCCAGA TCCCACCCAC CTTGCAGTGG CTTTCTTGTC ATCAGAGTAG AGAATGCACA    3109
GGTGTTGGTG AGGGCGTGTG GCTGAGCACT ACATGTCAAG TCAGAGTCAG TTTCTATCCA    3169
ATTCTC                                                              3175
```

(2) INFORMATION FOR SEQ ID NO:2:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO:2:

|  |  |  |  |  |  |  |  |  |  |  |  |  |  |  |
|---|---|---|---|---|---|---|---|---|---|---|---|---|---|---|
| Met<br>1 | Ala | Met | Asp | Glu<br>5 | Tyr | Leu | Trp | Met | Val<br>10 | Ile | Leu | Gly | Phe | Ile<br>15 | Ile |
| Ala | Phe | Ile | Leu<br>20 | Ala | Phe | Ser | Val | Gly<br>25 | Ala | Asn | Asp | Val | Ala<br>30 | Asn | Ser |
| Phe | Gly | Thr<br>35 | Ala | Val | Gly | Ser | Gly<br>40 | Val | Val | Thr | Leu | Arg<br>45 | Gln | Ala | Cys |
| Ile | Leu | Ala<br>50 | Ser | Ile | Phe | Glu | Thr<br>55 | Thr | Gly | Ser | Val | Leu<br>60 | Leu | Gly | Ala |
| Lys<br>65 | Val | Gly | Glu | Thr | Ile<br>70 | Arg | Lys | Gly | Ile | Ile<br>75 | Asp | Val | Asn | Leu | Tyr<br>80 |
| Asn | Glu | Thr | Val | Glu<br>85 | Thr | Leu | Met | Ala | Gly<br>90 | Glu | Val | Ser | Ala | Met<br>95 | Val |

-continued

| | | | | | | | | | | | | | | | |
|---|---|---|---|---|---|---|---|---|---|---|---|---|---|---|---|
|Gly|Ser|Ala|Val|Trp|Gln|Leu|Ile|Ala|Ser|Phe|Leu|Arg|Leu|Pro|Ile|
| | | |100| | | |105| | | |110| | | | |
|Ser|Gly|Thr|His|Cys|Ile|Val|Gly|Ser|Thr|Ile|Gly|Phe|Ser|Leu|Val|
| | |115| | | |120| | | |125| | | | | |
|Ala|Ile|Gly|Thr|Lys|Gly|Val|Gln|Trp|Met|Glu|Leu|Val|Lys|Ile|Val|
| |130| | | |135| | | |140| | | | | | |
|Ala|Ser|Trp|Phe|Ile|Ser|Pro|Leu|Leu|Ser|Gly|Phe|Met|Ser|Gly|Leu|
|145| | | |150| | | |155| | | | | | |160|
|Leu|Phe|Val|Leu|Ile|Arg|Ile|Phe|Ile|Leu|Lys|Lys|Glu|Asp|Pro|Val|
| | | |165| | | |170| | | |175| | | | |
|Pro|Asn|Gly|Leu|Arg|Ala|Leu|Pro|Val|Phe|Tyr|Ala|Ala|Thr|Ile|Ala|
| | |180| | | |185| | | |190| | | | | |
|Ile|Asn|Val|Phe|Ser|Ile|Met|Tyr|Thr|Gly|Ala|Pro|Val|Leu|Gly|Leu|
| |195| | | |200| | | |205| | | | | | |
|Val|Leu|Pro|Met|Trp|Ala|Ile|Ala|Leu|Ile|Ser|Phe|Gly|Val|Ala|Leu|
| |210| | | |215| | | |220| | | | | | |
|Leu|Phe|Ala|Phe|Phe|Val|Trp|Leu|Phe|Val|Cys|Pro|Trp|Met|Arg|Arg|
|225| | | |230| | | |235| | | | | | |240|
|Lys|Ile|Thr|Gly|Lys|Leu|Gln|Lys|Glu|Gly|Ala|Leu|Ser|Arg|Val|Ser|
| | | |245| | | |250| | | |255| | | | |
|Asp|Glu|Ser|Leu|Ser|Lys|Val|Gln|Glu|Ala|Glu|Ser|Pro|Val|Phe|Lys|
| | |260| | | |265| | | |270| | | | | |
|Glu|Leu|Pro|Gly|Ala|Lys|Ala|Asn|Asp|Asp|Ser|Thr|Ile|Pro|Leu|Thr|
| |275| | | |280| | | |285| | | | | | |
|Gly|Ala|Ala|Gly|Glu|Thr|Leu|Gly|Thr|Ser|Glu|Gly|Thr|Ser|Ala|Gly|
|290| | | |295| | | |300| | | | | | | |
|Ser|His|Pro|Arg|Ala|Ala|Tyr|Gly|Arg|Ala|Leu|Ser|Met|Thr|His|Gly|
|305| | | |310| | | |315| | | | | | |320|
|Ser|Val|Lys|Ser|Pro|Ile|Ser|Asn|Gly|Thr|Phe|Gly|Phe|Asp|Gly|His|
| | | |325| | | |330| | | |335| | | | |
|Thr|Arg|Ser|Asp|Gly|His|Val|Tyr|His|Thr|Val|His|Lys|Asp|Ser|Gly|
| | |340| | | |345| | | |350| | | | | |
|Leu|Tyr|Lys|Asp|Leu|Leu|His|Lys|Ile|His|Ile|Asp|Arg|Gly|Pro|Glu|
| |355| | | |360| | | |365| | | | | | |
|Glu|Lys|Pro|Ala|Gln|Glu|Ser|Asn|Tyr|Arg|Leu|Leu|Arg|Arg|Asn|Asn|
|370| | | |375| | | |380| | | | | | | |
|Ser|Tyr|Thr|Cys|Tyr|Thr|Ala|Ala|Ile|Cys|Gly|Leu|Pro|Val|His|Ala|
|385| | | |390| | | |395| | | | | | |400|
|Thr|Phe|Arg|Ala|Ala|Asp|Ser|Ser|Ala|Pro|Glu|Asp|Ser|Glu|Lys|Leu|
| | | |405| | | |410| | | |415| | | | |
|Val|Gly|Asp|Thr|Val|Ser|Tyr|Ser|Lys|Lys|Arg|Leu|Arg|Tyr|Asp|Ser|
| | |420| | | |425| | | |430| | | | | |
|Tyr|Ser|Ser|Tyr|Cys|Asn|Ala|Val|Ala|Glu|Ala|Glu|Ile|Glu|Ala|Glu|
| | |435| | | |440| | | |445| | | | | |
|Glu|Gly|Gly|Val|Glu|Met|Lys|Leu|Ala|Ser|Glu|Leu|Ala|Asp|Pro|Asp|
| |450| | | |455| | | |460| | | | | | |
|Gln|Pro|Arg|Glu|Asp|Pro|Ala|Glu|Glu|Lys|Glu|Glu|Lys|Asp|Ala|
|465| | | |470| | | |475| | | | | | |480|
|Pro|Glu|Val|His|Leu|Leu|Phe|His|Phe|Leu|Gln|Val|Leu|Thr|Ala|Cys|
| | | |485| | | |490| | | |495| | | | |
|Phe|Gly|Ser|Phe|Ala|His|Gly|Gly|Asn|Asp|Val|Ser|Asn|Ala|Ile|Gly|
| | |500| | | |505| | | |510| | | | | |
|Pro|Leu|Val|Ala|Leu|Trp|Leu|Ile|Tyr|Lys|Gln|Gly|Gly|Val|Thr|Gln|

|  |  |  | 515 |  |  |  | 520 |  |  |  | 525 |  |  |  |
|---|---|---|---|---|---|---|---|---|---|---|---|---|---|---|
| Glu | Ala 530 | Ala | Thr | Pro | Val | Trp 535 | Leu | Leu | Phe | Tyr | Gly 540 | Gly | Val | Gly | Ile |
| Cys 545 | Thr | Gly | Leu | Trp | Val 550 | Trp | Gly | Arg | Arg | Val 555 | Ile | Gln | Thr | Met | Gly 560 |
| Lys | Asp | Leu | Thr | Pro 565 | Ile | Thr | Pro | Ser | Ser 570 | Gly | Phe | Thr | Ile | Glu 575 | Leu |
| Ala | Ser | Ala | Phe 580 | Thr | Val | Val | Ile | Ala 585 | Ser | Asn | Ile | Gly | Leu 590 | Pro | Val |
| Ser | Thr | Thr 595 | His | Cys | Lys | Val | Gly 600 | Ser | Val | Val | Ala | Val 605 | Gly | Trp | Ile |
| Arg | Ser 610 | Arg | Lys | Ala | Val | Asp 615 | Trp | Arg | Leu | Phe | Arg 620 | Asn | Ile | Phe | Val |
| Ala 625 | Trp | Phe | Val | Thr | Val 630 | Pro | Val | Ala | Gly | Leu 635 | Phe | Ser | Ala | Ala | Val 640 |
| Met | Ala | Leu | Leu | Met 645 | Tyr | Gly | Ile | Leu | Pro 650 | Tyr | Val |  |  |  |  |